Figure 1:
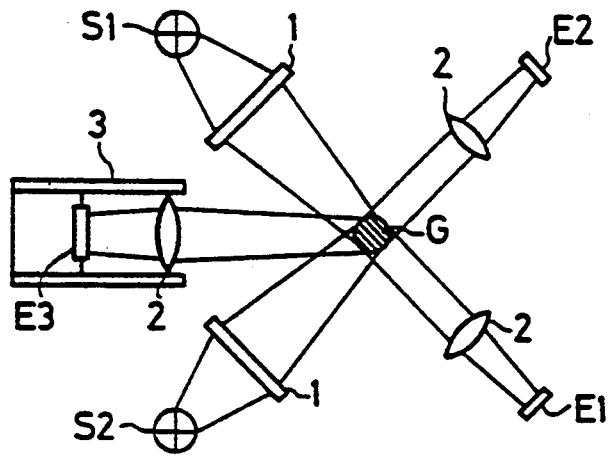

United States Patent

Joss et al.

[11] Patent Number: 5,414,520
[45] Date of Patent: May 9, 1995

[54] PROCESS AND DEVICE FOR DETECTING IMPURITIES IN A TEXTILE TEST MATERIAL

[75] Inventors: Rolf Joss, Dällikon; Hans Wampfler, Zürich, both of Switzerland

[73] Assignee: Zellweger Uster AG, Uster, Switzerland

[21] Appl. No.: 146,162

[22] PCT Filed: Mar. 15, 1993

[86] PCT No.: PCT/CH93/00071
§ 371 Date: Nov. 15, 1993
§ 102(e) Date: Nov. 15, 1993

[87] PCT Pub. No.: WO93/19359
PCT Pub. Date: Sep. 30, 1993

[30] Foreign Application Priority Data
Mar. 17, 1992 [CH] Switzerland .................. 855/92

[51] Int. Cl.[6] .................. G01N 21/89; G01N 33/36
[52] U.S. Cl. .................. 356/430; 356/238
[58] Field of Search .................. 356/238, 51, 429, 430, 356/384, 385; 250/562, 572

[56] References Cited

U.S. PATENT DOCUMENTS

| | | |
|---|---|---|
| 3,461,299 | 8/1969 | Felix . |
| 3,582,661 | 6/1971 | Pijls .................. 356/429 |
| 4,095,905 | 6/1978 | Kuni et al. .................. 356/430 |
| 4,739,176 | 4/1988 | Allen et al. .................. 250/572 |
| 4,887,155 | 12/1989 | Massen . |
| 4,948,260 | 8/1990 | Felix et al. .................. 356/429 |
| 5,054,317 | 10/1991 | Laubscher .................. 250/561 |

FOREIGN PATENT DOCUMENTS

| | | |
|---|---|---|
| 0399945 | 11/1990 | European Pat. Off. . |
| 2064106 | 6/1981 | United Kingdom .................. 356/238 |

*Primary Examiner*—Richard A. Rosenberger
*Attorney, Agent, or Firm*—Burns, Doane, Swecker & Mathis

[57] ABSTRACT

The test sample (G) is illuminated at at least two points (S 1, S2) and the reflection from the test sample (G) and also the diameter of the sample or the change therein are measured by receivers (E1, E2). The measurement signals thus obtained are linked together and the signal resulting from this process is examined for differences from a predetermined value. If a difference is detected, there is an impurity in the test sample (G). For use in combination with an electronic yarn clearer for the detection of foreign fibers in yarns.

22 Claims, 1 Drawing Sheet

PROCESS AND DEVICE FOR DETECTING IMPURITIES IN A TEXTILE TEST MATERIAL

The present invention relates to a process for detecting impurities in a textile test material of the yarn, roving or sliver type, in which the test material is subjected to light, the light reflected from the test material is measured and the presence of an impurity is indicated by a change of the reflected light.

In a process of this type known from EP-B-0,197,763, a background surrounding the test material in the manner of a guide slot and likewise subjected to light is provided. The background is co-ordinated with the test material in such a way that the total quantity of light reflected from the test material and of light coming from the background is dependent on the dimensions and density of the test material and on the distribution of the fibers within this. It is thereby possible for a variation in the reflected light to indicate an impurity and not a variation in the dimensions, or in the density or in the fiber distribution in the textile product.

Apart from the fact that in this process, whenever the kind or type of test material is changed, adjustment work involving a relatively high outlay is necessary to adapt the background to the test material, this process is also highly sensitive to the contamination and aging of the background. Moreover, both of these are phenomena which are unavoidable in a textile concern and which constantly occur in that very environment.

Now the invention is to provide a process which requires no coordination of the background with a test material and in which the possibility of any faults caused by the background is therefore prevented.

This object is achieved, according to the invention, in that the test material is illuminated at at least two points, and in addition to the reflection the diameter of the test material or its change is measured, and in that the measurement signals thus obtained are interlinked.

The invention proceeds, therefore, from the fact that the light reflected from a given test material of a given diameter is constant as long as the degree of reflection of the test material does not change, that is to say the latter contains no impurities. The change of the degree of reflection and consequently the presence of impurities, especially of foreign fibers, can then be detected by forming a quantity from the reflection signal and from the diameter signal and by analysing this quantity.

Accordingly, a preferred embodiment of the process according to the invention is characterized in that a quotient is derived from the reflection signal and from the diameter signal and is checked continuously for deviations from an average value.

The invention relates, furthermore, to a device for carrying out said process, with transmission means for illuminating the test material, with reception means for measuring the light reflected and/or absorbed by the test material, and with means for evaluating the measurement signals.

The device according to the invention is characterized in that the transmission means are designed in such a way that a simultaneous illumination of a plurality of points located on the same portion of test material or a multiple illumination of the test material at the same point takes place, and in that reception means are provided for the light reflected and/or attenuated by the test material at said points.

Figure 2:
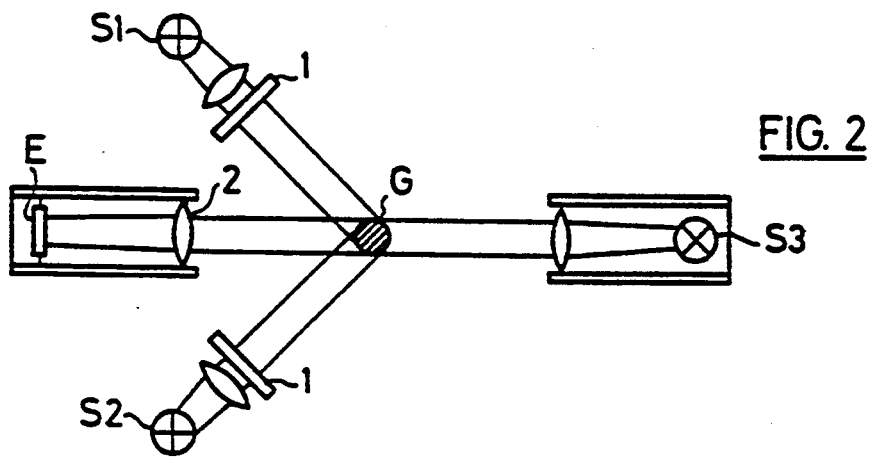
Figure 3:
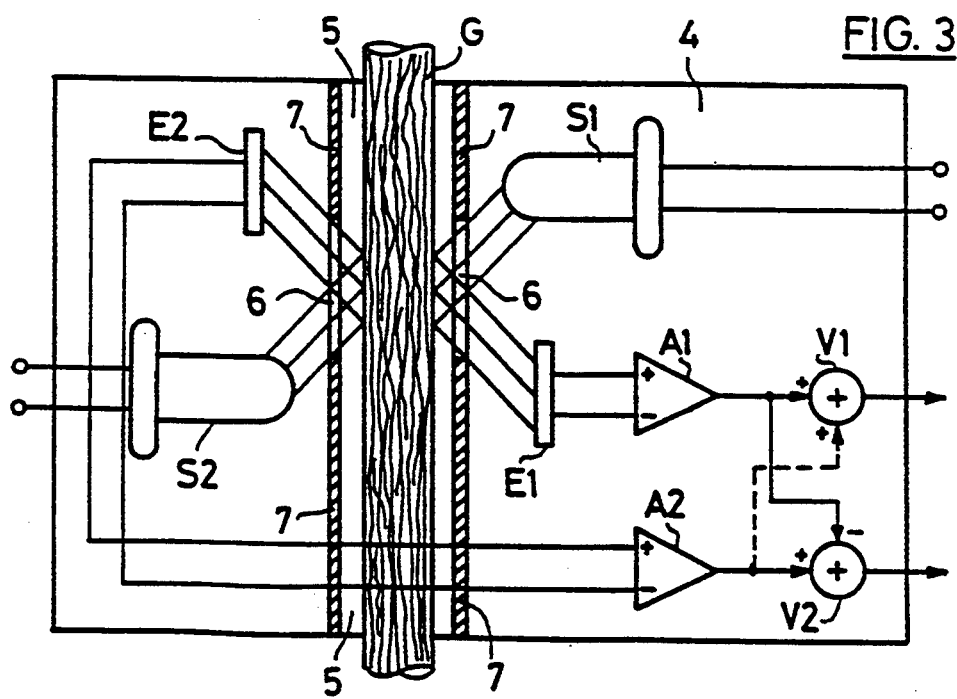

The invention is explained in more detail below by means of three exemplary embodiments and the drawings; in these:

FIG. 1 shows a diagrammatic representation of a first exemplary embodiment of a device according to the invention, FIG. 2 shows a diagrammatic representation of a second exemplary embodiment, and FIG. 3 shows a representation of a third exemplary embodiment of a device according to the invention.

In the exemplary embodiments illustrated in FIGS. 1 and 2, a simultaneous measurement of the yarn diameter and of the reflection on a yarn G is carried out, the measurement signals relating to the same yarn point. The measuring zone is no larger than 0.5 mm. This is because a typical foreign fiber is wound round the yarn, and a typical value for the yarn twist is around 1000 twists per meter. Instead of simultaneous measurement at one yarn point, it is also possible to measure at two points X and Y, store the result of the earlier point X and synchronize the measurements in such a way that measurement takes place at the point Y exactly when the measuring zone of the yarn, measured previously at X, runs through this.

A quotient is formed from these two signals for the reflection and the diameter, and in contrast to the reflection proportional to the yarn diameter, this quotient, if the degree of reflection of the yarn remains constant, is independent of possible fluctuations in diameter. Since the degree of reflection is dependent on the fiber material, said quotient remains constant until a fault having a degree of reflection different from that of the fiber material, that is to say, for example, a foreign fiber, passes the measuring point. The value of the reflection-by-diameter quotient can be found by continuous averaging over relatively long pieces of yarn. This reference value is assigned corresponding trigger threshold values, and when these are exceeded by the measurement signal this indicates respectively a foreign fiber or another impurity which is lighter or darker than the fiber material under consideration.

The measurement of the diameter preferably takes place optically in the same way as the reflection measurement, specifically by direct light, or by transmitted light using a shading method. In the latter instance, a slightly diffuse illumination is more suitable than parallel light guidance, since the decrease in intensity at the edge of the yarn is better compensated thereby. A large-area diffuse illumination is preferably employed, and by means of this the curved yarn surface is illuminated uniformly from as large a spatial angle as possible.

The diameter of the yarn can, of course, also be measured capacitively, in which case a combined measuring head of the type described in EP-A-0,401,600 is preferably used. The measuring arrangement can also be modified in such a way that further parameters, such as, for example, hairiness, can also be measured in addition. In this case, an additional dark-field illumination, such as is described by way of example in EP-A-0,226,843, is recommended in order to compensate for the decrease in intensity at the edge of the yarn.

Because the contrasts are generally more clearly visible in short-wave light than in long-wave light, short-wave light is preferably used. On the other hand, there are also fibers in which the foreign fibers occurring most frequently have a high absorption in the infrared range. In these instances, it is expedient to use correspondingly long-wave light. Luminous diodes are preferably employed as light sources, because they are long-lived and stable and, moreover, can easily be modulated. Photodiodes or photomultipliers are used as receivers.

In the exemplary embodiment illustrated in FIG. 1, two transmitters S1 and S2 and three receivers E1, E2 and E3 are provided, the receivers E1 and E2 measuring the diameter of the yarn G and the receiver E3 the reflection. Reference symbol 1 denotes diffusing discs arranged in the beam path shortly after the transmitters, and reference symbol 2 denotes convergent lenses arranged in the beam path shortly before the receivers. At least the receiver E3 for the light reflected from the yarn G is installed in a housing 3 for screening against disturbing environmental influences, such as extraneous light and the like.

In the exemplary embodiment of FIG. 2, three transmitters S1, S2 and S3, but only one receiver E, are used. The transmitters S1 and S2 illuminate the yarn G with diffuse light, and the receiver E measures on the one hand the reflected light and on the other hand the transmitted light which comes from the light source S3 and which is used for determining the diameter. The separation of the two simultaneously incident types of light is carried out either by a time-division multiplex process or by modulation, in the latter instance the transmitters S1 and S2 for the reflected light being modulated differently from the transmitter S3 for the transmitted light, and the fractions being separated by appropriate demodulation.

In the exemplary embodiment illustrated in FIG. 3, two reflected-light photocouplers S1, E1 and S2, E2, which sense the yarn G on sides located opposite one another, are provided. The photocouplers are provided on both sides of a measuring slot or measuring gap 5 which is formed in a housing 4 and through which the yarn G runs and which has, in the region of the photocouplers, optically transparent apertures 6 for the passage of the light beams. The two photocouplers S1, E1 and S2, E2 are so arranged that the transmitter of one photocouplers is located respectively opposite the receiver of the other photocoupler. Any transmitted light between the two photocouplers, that is to say between S1 and E2 and/or between S2 and E1, is prevented by the dimensioning of the apertures 6. Or in other words, the parts 7 of the side walls of the measuring gap 5 which are adjacent to the apertures 6 at the top and bottom act as a diaphragm to prevent transmitted light from the transmitter S1 to the receiver E2 and from the transmitter S2 to the receiver E1 respectively.

Each of the two photocouplers forms a measuring channel, the output signal of which represents a quantity proportional to the diameter of the yarn G under consideration. If the output signals of the two channels are interlinked and one signal is subtracted from the other, this subtraction signal, when it exceeds or falls below a band range around zero, gives an indication as to the presence of an impurity.

Each of the two channels contains an amplifier A1 and A2 connected to the respective receiver E1, E2 and at least one of the channels contains a logic element connected to the amplifier and intended for linking the signals of the two channels. This logic element, which supplies an impurity signal at its output, is designated in FIG. 3 by the reference signal V2. The logic element V1 shown in the channel containing the receiver E1 and the amplifier A1 is optional and does not necessarily have to be present. If it is present, it serves for adding the output signals of the two channels and thus supplies, as does each channel on its own, a signal which is proportional to the yarn diameter and from which the yarn diameter can be derived after appropriate calibration.

If the diaphragms 7 are omitted and if the apertures 6 are appropriately enlarged, a determination of the yarn diameter by transmitted light can take place between S1 and E2 and/or between S2 and E1. In this case, the two reflected-light barriers would work by time-division multiplex.

The devices, described with reference to FIGS. 1 to 3, for detecting impurities in a yarn is designed as a compact measuring head and is preferably used in combination with an electronic yarn clearer (see EP-B-0,197,763 in this respect), the cutting device of which is also controlled, in addition to the measuring head of the cleaner, by the measuring head for impurities.

As already mentioned, a plurality of functions, that is to say, for example, yarn clearer, hairiness measurement and the detection of foreign fibers, can be performed by means of a single optical sensing device. It is also possible, with a combined capacitive/optical measuring member, to measure capacitively the yarn faults for the purpose of yarn clearer and optically the hairiness and the reflection representative of foreign fibers.

We claim:

1. A process for detecting impurities in a textile test material, comprising the steps of:
   illuminating the test material with light; measuring light reflected by the test material to produce a reflection signal;
   producing a diameter signal indicative of changes in the diameter of the test material;
   combining the reflection signal and the diameter signal to produce a measurement value; and
   detecting changes in the measurement value to indicate the presence of an impurity in the test material.

2. Process according to claim 1, characterized in that a quotient is derived from the reflection signal and from the diameter signal and is checked continuously for deviations from an average value.

3. Process according to claim 2, further including the step of using the diameter signal to detect yarn faults the purpose of yarn clearing.

4. Process according to claim 2, further including the step of using the reflection signal to measure the hairiness of the test material.

5. Process according to claim 2, characterized in that the diameter signal is obtained from the light reflected by the test material.

6. Process according to claim 2, characterized in that the diameter signal is obtained by transmitted light using a shading method.

7. Process according to claim 2, characterized in that said average value is determined adaptively by continuous averaging over relatively large lengths of the test material.

8. The process of claim 1, wherein said diameter signal is indicative of changes in the diameter of the portion of the test material which is illuminated with said light.

9. The process of claim 1 wherein said step of illuminating the test material with light includes illuminating a portion of the test material from at least two different directions.

10. The process of claim 1 wherein said step of illuminating the test material with light includes illuminating a portion of the test material with light from at least two light sources.

11. A device for the detection of impurities in a textile test material, comprising:
light source means for producing multiple illuminations of the test material;
means for receiving and measuring light reflected and/or attenuated by the test material for each of said multiple illuminations;
means for detecting the diameter of the test material from the measurements obtained from at least one of said illuminations; and means for comparing the measured light reflected by the test material to the diameter of the test material, to thereby detect impurities in the test material.

12. The device of claim 11 wherein said light source means simultaneously illuminates a plurality of points located on the same portion of the test material.

13. The device of claim 11 wherein said light source means illuminates the same point on the test material from a plurality of light sources.

14. The device of claim 11 wherein said light source means includes two light transmitters and said light receiving and measuring means includes three light receivers, wherein two of said light receivers are located on sides of the test material opposite said two light transmitters, respectively, for measuring transmitted light, and the third light receiver is located on the same side of the test material as said light transmitters for measuring light reflected from the test material.

15. The device of claim 11 wherein said light source means comprises two light transmitters located on one side of the test material and a third light transmitter located on the other side of the test material, and said light receiving and measuring means includes a light receiver located on said one side of the test material for receiving light from said two light transmitters that is reflected by the test material and light transmitted by said third light source, and further including means for controlling the light from said transmitters to separate the reception of transmitted light from the reception of reflected light.

16. The device of claim 15 wherein said controlling comprises modulation of the light from said transmitters.

17. The device of claim 15 wherein said controlling comprises time-division multiplexing of the light from said transmitters.

18. The device of claim 11 wherein said light source means and said light receiving means comprise a pair of reflected light photocouplers located on opposite sides of the test material.

19. The device of claim 18 wherein each photocoupler includes a light transmitter and a light receiver, and wherein said photocouplers are arranged such that the light receiver of each photocoupler is disposed to receive light transmitted from the light transmitter of the other photocoupler, and means for time-division multiplexing the light transmitted from each of said photocouplers.

20. The device of claim 11 wherein said light source means and said light receiving and measuring means form part of a measuring head for electronic yarn clearing and/or hairiness measurement.

21. The device of claim 11 wherein said comparing means determines the quotient of measured reflected light and the detected diameter of the test material, and compares said quotient to an average value.

22. The device of claim 21 wherein said average value is determined by averaging said quotient over a period of time.

* * * * *

UNITED STATES PATENT AND TRADEMARK OFFICE
CERTIFICATE OF CORRECTION

PATENT NO. : 5,414,520

DATED : May 9, 1995

INVENTOR(S) : Rolf JOSS and Hans WAMPFLER

It is certified that error appears in the above-indentified patent and that said Letters Patent is hereby corrected as shown below:

ON THE TITLE PAGE:

[21] Appl. No.: Change "146,162" to --146,163--.

Signed and Sealed this

Eleventh Day of July, 1995

Attest:

BRUCE LEHMAN

*Attesting Officer*  *Commissioner of Patents and Trademarks*